US011974941B2

United States Patent
Shiino (10) Patent No.: US 11,974,941 B2
(45) Date of Patent: May 7, 2024

(54) INTRAORAL DEVICE

(71) Applicant: Hiromi Shiino, Chiba (JP)

(72) Inventor: Hiromi Shiino, Chiba (JP)

(73) Assignee: Hiromi Shiino, Chiba (JP)

( * ) Notice: Subject to any disclaimer, the term of this patent is extended or adjusted under 35 U.S.C. 154(b) by 0 days.

(21) Appl. No.: 18/035,653

(22) PCT Filed: Dec. 28, 2021

(86) PCT No.: PCT/JP2021/048725
§ 371 (c)(1),
(2) Date: May 5, 2023

(87) PCT Pub. No.: WO2023/127071
PCT Pub. Date: Jul. 6, 2023

(65) Prior Publication Data
US 2023/0301822 A1    Sep. 28, 2023

(51) Int. Cl.
*A61F 5/56*    (2006.01)
*A61C 7/08*    (2006.01)

(52) U.S. Cl.
CPC .................................. *A61F 5/566* (2013.01)

(58) Field of Classification Search
CPC ......... A61F 5/56–58; A61C 7/08; A61C 7/10; A61C 7/36; A63B 71/08; A63B 71/081; A63B 71/085; A63B 2071/086; A63B 2071/088
See application file for complete search history.

(56) References Cited

U.S. PATENT DOCUMENTS

| | | | | |
|---|---|---|---|---|
| 3,724,075 A * | 4/1973 | Kesling | ..................... | A61C 7/08 433/6 |
| 4,915,630 A * | 4/1990 | Honig | ..................... | A61C 5/007 433/215 |
| 5,915,385 A * | 6/1999 | Hakimi | ..................... | A61F 5/566 128/859 |
| 7,226,287 B2 * | 6/2007 | Abels | ..................... | A61C 7/00 433/18 |

(Continued)

FOREIGN PATENT DOCUMENTS

| JP | 11-507852 A | 7/1999 |
|---|---|---|
| JP | 2005-095218 A | 4/2005 |

(Continued)

OTHER PUBLICATIONS

Notice of Reasons for Refusal dated Jun. 9, 2022 corresponding to Japanese Patent Application No. 2022-528973, with English translation thereof.

(Continued)

*Primary Examiner* — Michelle J Lee
(74) *Attorney, Agent, or Firm* — SQUIRE PATTON BOGGS (US) LLP (57) ABSTRACT

An intraoral device having a main body to be attached to maxillary teeth, the main body including a first region, a second region, and a third region. Mandibular anterior teeth are in contact with the first region. The mandibular anterior teeth in contact with the first region are moved toward the third region while being kept in contact with the second region, which causes the mandible to move anteriorly and superiorly.

5 Claims, 9 Drawing Sheets

(56) References Cited

U.S. PATENT DOCUMENTS

| | | | |
|---|---|---|---|
| 7,730,890 B2 * | 6/2010 | Enoch | A61F 5/566 128/848 |
| 7,730,891 B2 * | 6/2010 | Lamberg | A61F 5/566 128/848 |
| 2007/0079833 A1 | 4/2007 | Lamberg | |
| 2008/0099029 A1 | 5/2008 | Lamberg | |

FOREIGN PATENT DOCUMENTS

| | | |
|---|---|---|
| JP | 3129305 U | 2/2007 |
| JP | 3177755 U | 8/2012 |
| JP | 3200349 U | 10/2015 |
| JP | 3205183 U | 7/2016 |

OTHER PUBLICATIONS

Decision to Grant a Patent dated Oct. 21, 2022 corresponding to Japanese Patent Application No. 2022-528973, with English translation thereof.

"TMJ Splint Therapy Handbook"; Society of Temporomandibular Joint Clinicians, Yasuo Shiraishi; Ishiyaku Publishers, Inc.; 1st Edition, 1st Printing Published: Jun. 10, 2016; 1st Edition, 2nd Printing Published: Jun. 10, 2019. pp. 1-288.

* cited by examiner

INTRAORAL DEVICE

TECHNICAL FIELD

The present invention relates to an intraoral device.

BACKGROUND ART

Devices to be anchored to maxillary teeth have been proposed (see PTL 1 and 2).

CITATION LIST

Patent Literature

[PTL 1] Japanese Utility Model Registration No. 3177755
[PTL 2] Japanese Utility Model Registration No. 3205183

SUMMARY OF INVENTION

Technical Problem

An object in one embodiment of the present invention is to provide an intraoral device that keeps the tongue in its correct position where it should be.

Solution to Problem

The present invention includes the following embodiment.

An intraoral device including a main body attached to maxillary teeth, wherein
the main body includes a first region, a second region, and a third region,
anterior teeth of a mandible are in contact with the first region, and
the anterior teeth of the mandible in contact with the first region are moved toward the third region while being kept in contact with the second region, thereby causing the mandible to move anteriorly and superiorly.

Advantageous Effects of Invention

According to the embodiment of the present invention, an intraoral device that keeps the tongue in its correct position where it should be is provided.

DESCRIPTION OF EMBODIMENTS

Intraoral Device 10 According to Embodiment 1

Figure 1:
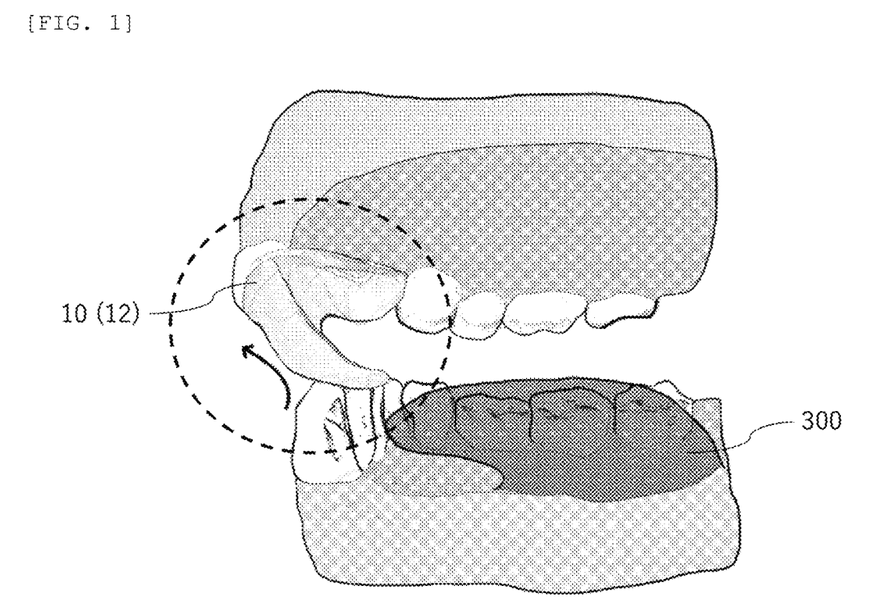
FIG. 1 is a cross-sectional view explaining how an intraoral device 10 according to Embodiment 1 is attached to maxillary teeth.
Figure 2:
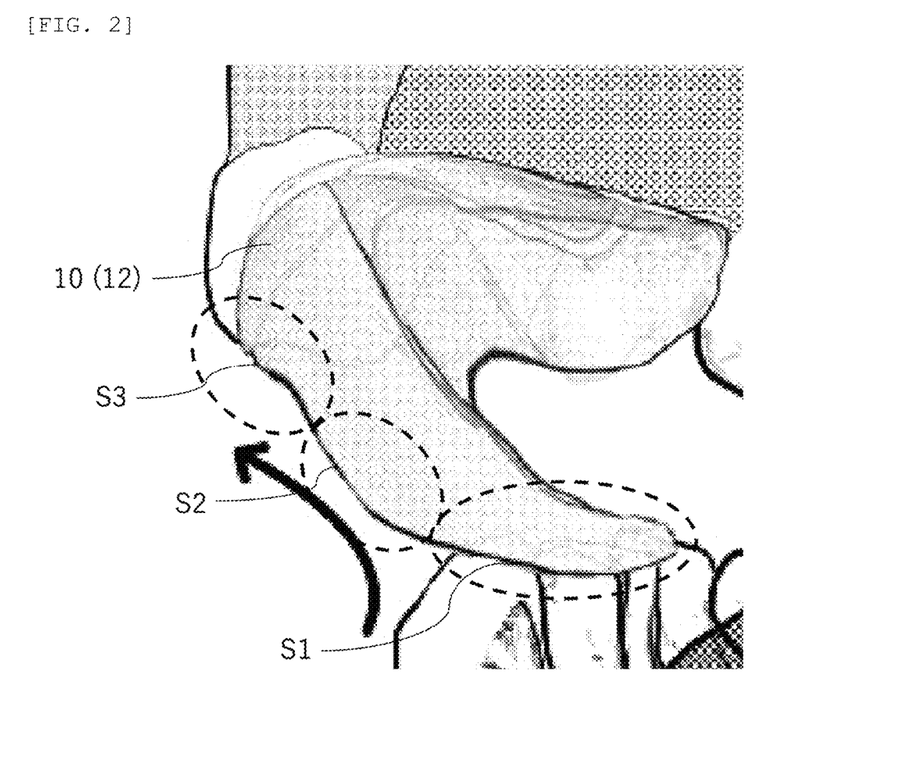
FIG. 2 is an enlarged view of parts encircled by dot lines in FIG. 1.
Figure 3:
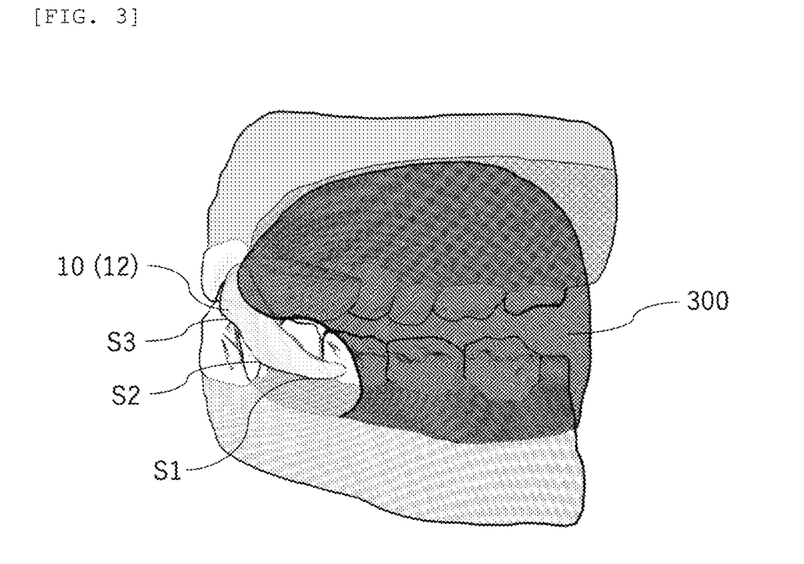
FIG. 3 is a diagram illustrating a condition after the mandibular anterior teeth in contact the first region S1 have been moved to the third region S3 while being kept in contact with the second region S2 (condition after the mandible has moved anteriorly and superiorly).

FIG. 1 is a diagram explaining how an intraoral device 10 according to Embodiment 1 is attached to maxillary teeth. FIG. 2 is an enlarged view of parts encircled by dot lines in FIG. 1. FIG. 3 is a diagram illustrating a condition after the mandibular anterior teeth in contact the first region S1 have been moved to the third region S3 while being kept in contact with the second region S2 (condition after the mandible has moved anteriorly and superiorly). In FIG. 2, the first region S1, second region S2, and third region S3 are each encircled by the dot line. The arrow in FIG. 1 and FIG. 2 indicates the direction of movement of the mandible. In FIG. 1 and FIG. 3, for easy understanding of the present invention, the tongue 300 is illustrated proportionally larger and thicker.

As shown in FIG. 1 to FIG. 3, the intraoral device 10 according to Embodiment 1 includes a main body 12 attached to maxillary teeth. The main body 12 includes a first region S1, a second region S2 and a third region S3. Mandibular anterior teeth are in contact with the first region S1. The intraoral device 10 causes the mandible to move anteriorly and superiorly by moving the mandibular anterior teeth in contact with the first region S1 toward the third region S3 while keeping the mandibular anterior teeth in contact with the second region S2. According to Embodiment 1, an intraoral device 10 that keeps the tongue 300 in its correct position where it should be is provided. A detailed description follows below.

(Intraoral Device 10)

An intraoral device 10 is an appliance worn inside an oral cavity. An oral cavity refers to the area from the mouth to the pharynx. The mouth can also be called an opening of an oral. A mouthpiece or splint is one example of the intraoral device 10. The "intraoral device 10" according to this embodiment has a shape that allows the mouth to be closed when being attached inside the oral cavity. An appliance that partly protrudes or is exposed from the mouth when the mouth is closed, or an appliance that does not allow the mouth to be closed when the appliance is attached, is not included in the herein defined "intraoral device" even though the appliance may be called a mouthpiece or splint.

(Main Body 12)

The intraoral device 10 includes a main body 12 attached to maxillary teeth. The main body 12 includes a first region S1, a second region S2 and a third region S3. The first region S1, second region S2, and third region S3 are each a partial area on the surface of the main body 12. A partial area can also be called a segment. The first to third regions S1 to S3 are different regions. One region on the surface of the main body 12 never be the first region S1 and at the same time the second region S2 or the third region S3. One region on the surface of the main body 12 never be the second region S2 and at the same time the third region S3. In other words, for example, if a region on the surface of the main body 12 is the first region S1, this region never be the second region S2 or the third region S3. The main body 12 should preferably have the first region S1, second region S2, and third region S3 in this order from inside outward of the oral cavity. The first region S1, second region S2, and third region S3 should preferably be continuous in this order to allow unhindered and smooth anterior and superior movement of the mandible.

(First Region S1)

The first region S1 is a region in contact with mandibular anterior teeth. In other words, a "region" in contact with mandibular anterior teeth, on the surface of the main body 12, is herein called the "first region S1." The main body 12 having such first region S1 allows the mandible to start moving easily. The first region S1, in addition to being a region in contact with mandibular anterior teeth, should preferably be a region positioned such that, with the mandibular anterior teeth in contact therewith, the mandible cannot retract further posteriorly from there. Namely, the main body 12 should preferably include a region designed such that, with the mandibular anterior teeth in contact therewith, the mandible cannot retract further posteriorly from there, and such a region particularly preferably designed in this manner is herein referred to as the first region S1. The main body 12 having such a region as the first region S1 can prevent accidental posterior movement of the mandible, and detachment of the mandibular anterior teeth from the first region S1. Thus the mandible can start the movement to be described later easily. The first region S1 should preferably be a region in contact with mandibular anterior teeth, in particular both of the left and right mandibular central incisors and lateral incisors, and should more preferably be a region not in contact with (or, not able to make contact with) other teeth than the left and right mandibular central incisors and lateral incisors.

(Second Region S2)

The main body 12 is formed in a shape that allows movement of the mandibular anterior teeth in contact with the first region S1 while being kept in contact with a certain "region," and this certain "region" is herein called the "second region S2." The main body 12, having such second region S2, is able to guide the mandibular anterior teeth in contact with the first region S1 toward the third region S3 in an unhindered and smooth manner.

(Third Region S3)

The mandibular anterior teeth in contact with the first region S1 is moved toward the third region S3 while being kept in contact with the second region S2, thereby causing the mandible to move anteriorly and superiorly (see the arrow in FIG. 1 and FIG. 2). The main body 12 is formed in a shape that causes the mandibular anterior teeth in contact with the first region S1 to move toward a certain "region" while being kept in contact with the second region S2 to move the mandible anteriorly and superiorly, and this certain "region" is herein called the "third region S3." The main body 12 having such third region S3 causes anterior and superior movement of the mandible so that the space between the maxillary and mandibular molars is widened and the intraoral volume is increased.

According to Embodiment 1 described above, the mandibular anterior teeth in contact with the first region S1 are moved toward the third region S3 while being kept in contact with the second region S2, to guide the mandibular anterior teeth in contact with the first region S1 toward the third region S3 in an unhindered and smooth manner, thereby to cause the mandible to move anteriorly and superiorly. In other words, the user can easily move the mandible anteriorly and superiorly only by wearing the intraoral device 10 according to this embodiment. The anterior and superior movement of the mandible widens the space between the maxillary and mandibular molars and enlarges the intraoral volume. This way, the user of the intraoral device 10 is encouraged to place a distal end portion of the tongue 300 at its correct position where it should be (on the lingual side face of the main body 12, preferably the incisive papilla) so that the entire tongue 300 can be guided to and placed in its correct position where it should be (where the tongue 300 makes tight contact with the palate, i.e., allows easy nasal breathing). In other words, the intraoral device 10 according to Embodiment 1 can indicate the user of the intraoral device 10 the correct position where it should be of the distal end portion of the tongue 300 and guide the user's tongue 300 to the correct position where it should be. According to this embodiment, the user of the intraoral device 10 can readily place the tongue 300 in its correct position where it should be (where the tongue 300 makes tight contact with the palate, i.e., allows easy nasal breathing), so that the user can naturally bring the tongue 300 into contact with the palate and make this tongue contact a habit. This means that the oral breathing path (i.e., oral cavity) is closed by the tongue 300, which encourages the user of the intraoral device 10 to breathe through the nose. Breathing through the nose rather than the mouth can increase salivary secretion. Therefore, the intraoral device 10 according to this embodiment is also effective for treatment of periodontal diseases. Moreover, the anterior and superior movement of the mandible can prevent back teeth clenching and therefore the intraoral device 10 according to this embodiment is also effective for treatment of hyperesthesia and temporomandibular joint disorders.

Figure 4A:
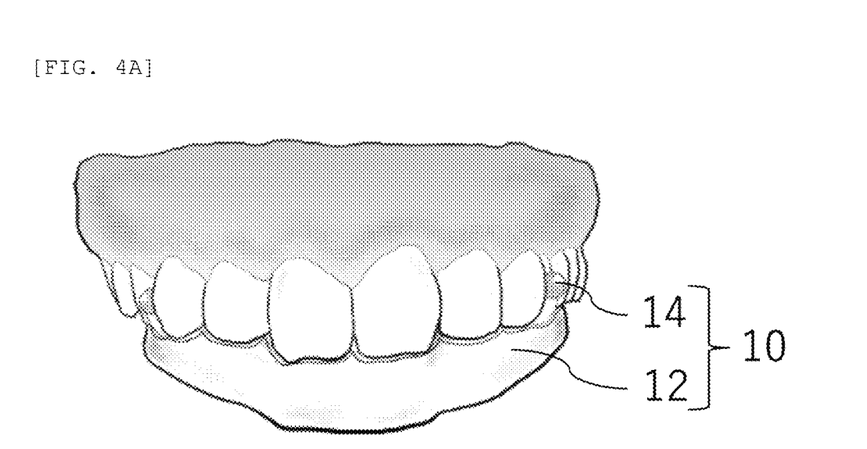
FIG. 4A is a front view explaining how the intraoral device 10 according to Embodiment 1 is attached to maxillary teeth.
Figure 4B:
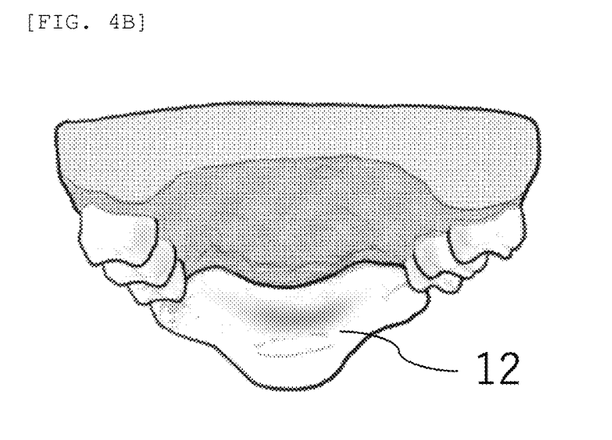
FIG. 4B is a rear view explaining how the intraoral device 10 according to Embodiment 1 is attached to maxillary teeth.
Figure 4C:
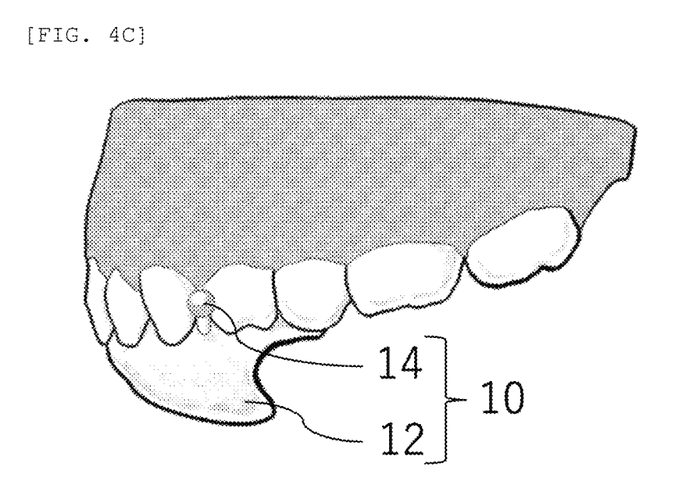
FIG. 4C is a side view explaining how the intraoral device 10 according to Embodiment 1 is attached to maxillary teeth.

FIG. 4A is a front view explaining how the intraoral device 10 according to Embodiment 1 is attached to maxillary teeth. FIG. 4B is a rear view explaining how the intraoral device 10 according to Embodiment 1 is attached to maxillary teeth. FIG. 4C is a side view explaining how the intraoral device 10 according to Embodiment 1 is attached to maxillary teeth. In FIG. 4A to FIG. 4C, the mandible and tongue are not shown. As shown in FIG. 4A to FIG. 4C, the main body 12 should preferably have a shape conforming to the maxillary teeth to which the main body 12 is attached. Namely, the main body 12 should preferably fit along an interface between crown and gingiva on the lingual side of the maxillary teeth to which the main body 12 is attached. This way, the incisive papilla is exposed from the main body 12 so that the distal end portion of the tongue can be positioned on the incisive papilla. Thus the user of the intraoral device 10 is encouraged to place the distal end portion of the tongue on the incisive papilla so that the entire tongue can be guided to and placed in its correct position where it should be (where the tongue makes tight contact with the palate, i.e., allows easy nasal breathing).

The maxillary teeth to which the main body 12 is attached should preferably be the teeth from the maxillary right first or second premolar to the maxillary left first or second premolar. This way, the volume of the oral cavity will be larger than if the main body 12 extends as far as to the back teeth, so that interference between the main body 12 and the tongue can be prevented. Thus the intraoral device 10 provided herein, while being compact and easy to handle for the user, can encourage the user to place the distal end portion of the tongue at its correct position where it should be (on the lingual side face of the main body 12, preferably the incisive papilla), and guide the user to place the entire tongue in its correct position where it should be (where the tongue makes tight contact with the palate, i.e., allows easy nasal breathing).

Figure 5A:
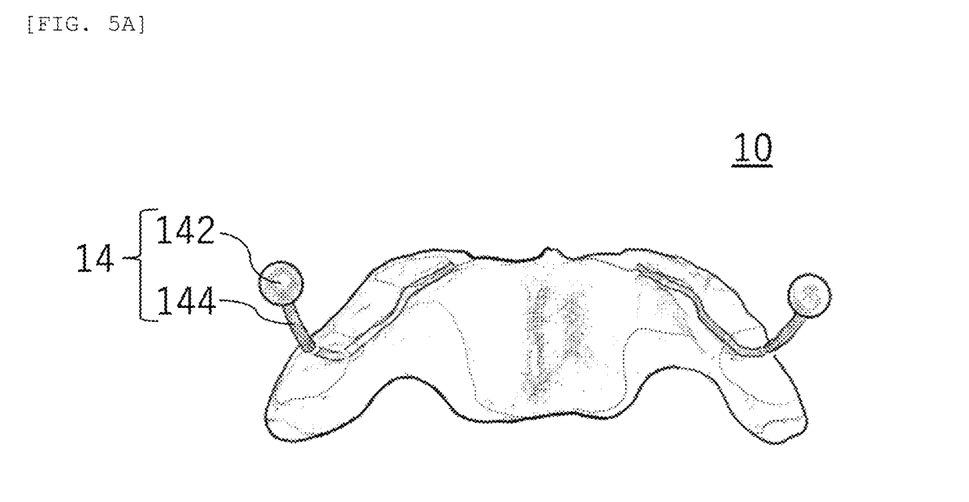
FIG. 5A is a rear view illustrating the intraoral device 10 according to Embodiment 1 (viewed from the palatal side).
Figure 5B:
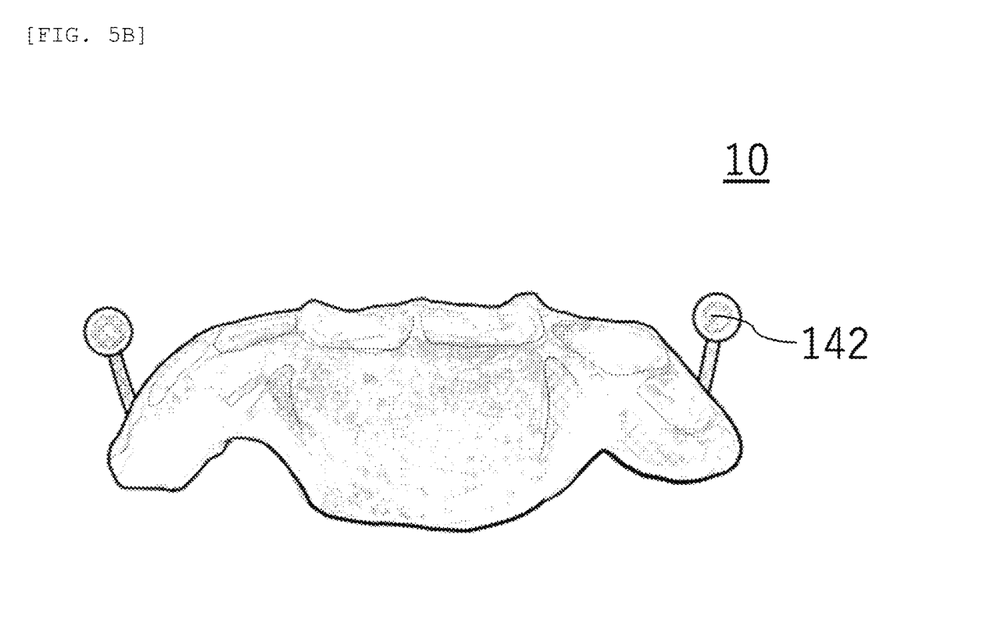
FIG. 5B is a front view illustrating the intraoral device 10 according to Embodiment 1 (viewed from the labial side).
Figure 5C:
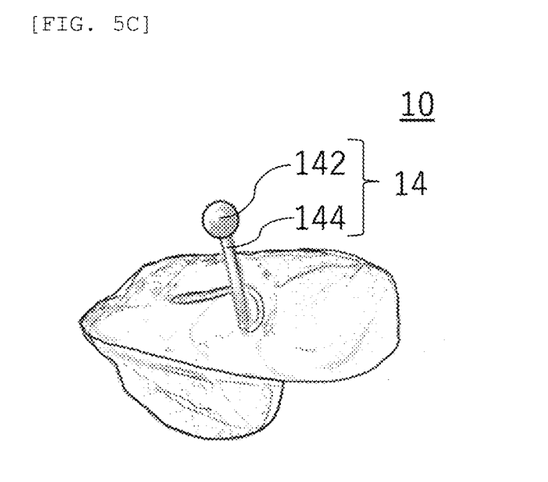
FIG. 5C is a side view illustrating the intraoral device 10 according to Embodiment 1.
Figure 5D:
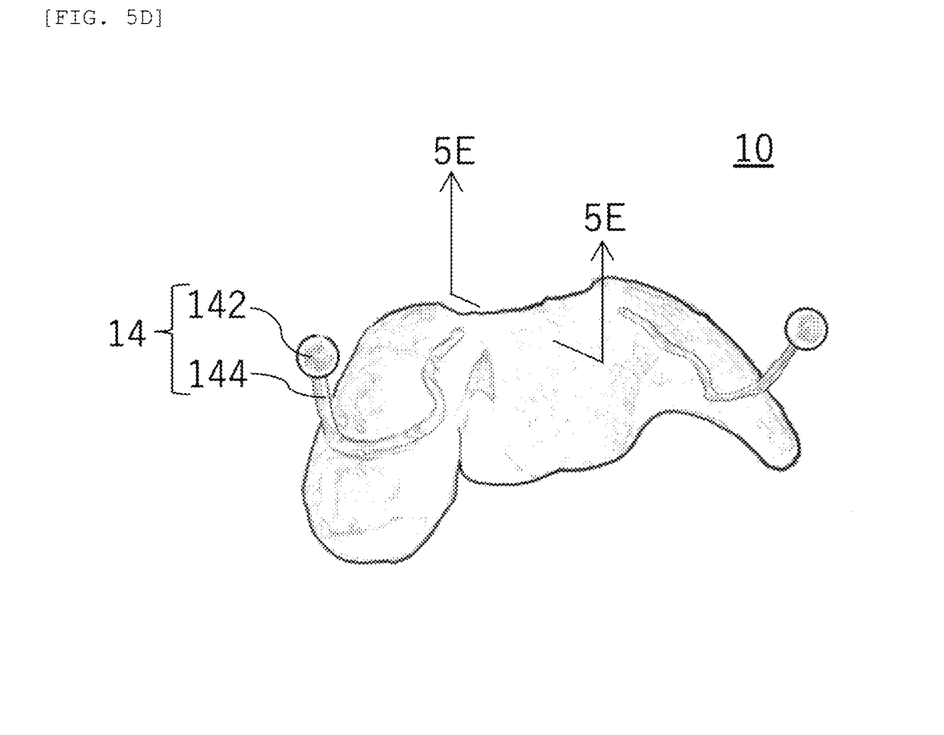
FIG. 5D is a perspective view illustrating the intraoral device 10 according to Embodiment 1.
Figure 5E:
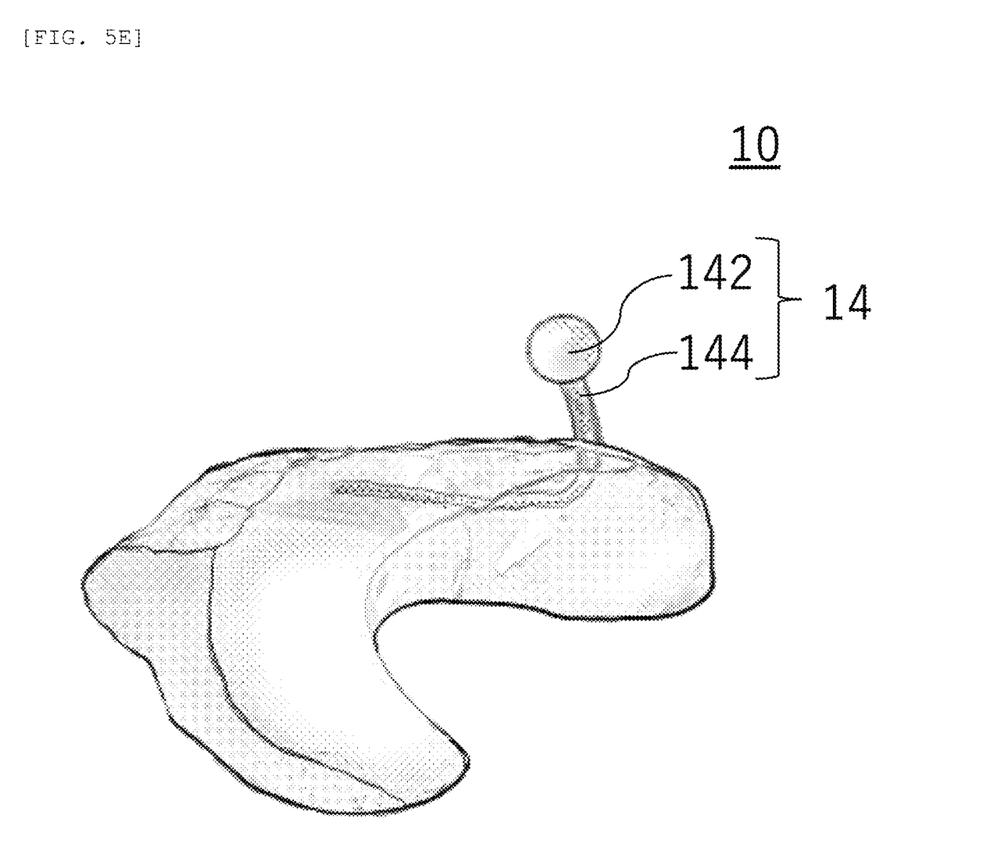
FIG. 5E is a cross-sectional view along line 5E-5E in FIG. 5D.

FIG. 5A is a rear view illustrating the intraoral device 10 according to Embodiment 1 (viewed from the palatal side). FIG. 5B is a front view illustrating the intraoral device 10 according to Embodiment 1 (viewed from the labial side). FIG. 5C is a side view illustrating the intraoral device 10 according to Embodiment 1. FIG. 5D is a perspective view illustrating the intraoral device 10 according to Embodiment 1. FIG. 5E is a cross-sectional view along line 5E-5E in FIG. 5D. As shown in FIG. 5A to FIG. 5E, the main body 12 should preferably have a locking device 14. The locking device 14 is an appliance that keeps the main body 12 inside the oral cavity. The locking device 14 should preferably include a hook 142 engaged with an undercut that exists in a direction in which the intraoral device 10 is attached and removed, and a leg portion 144. An undercut refers to a surface portion of a tooth that generates resistance in the direction of attachment and removal of the intraoral device 10. Among undercuts, preferably, the hook 142 should be engaged with one that exists between a maxillary canine and a second premolar.

Preferably, the leg portion 144 extends from the hook 142 and is embedded in the main body 12, entering the main body 12 at a point higher than the lingual crown center of a maxillary tooth (preferably canine or premolar) on the palatal side, passing through a point higher than the lingual crown center of a maxillary tooth (preferably lateral incisor) on the palatal side while being embedded in the main body 12, and terminating at a point higher than the lingual crown center of a maxillary tooth (preferably central incisor) on the palatal side. With the leg portion 144 configured in this manner, the lingual upper edge of the main body 12 can be positioned at the interface between crown and gingiva. In other words, in positioning the lingual upper edge of the main body 12 at the interface between crown and gingiva, the leg portion 144 does not get in the way. Thus the intraoral device 10 can encourage the user to place the distal end portion of the tongue on the incisive papilla and guide the user to place the entire tongue in its correct position where it should be (where the tongue makes tight contact with the palate).

The main body 12 should preferably be made of resin. The main body 12 made of resin will undergo wear by the friction between the mandibular anterior teeth and the intraoral device 10 into a shape that allows easier movement of the mandible, i.e., with the progress of use of the intraoral device 10, the shape of the main body 12 can be transformed into one that allows easier movement of the mandible. Resin material used for the main body 12 will allow easy correction of the shape of the main body 12 by a dentist even if the main body 12 has undergone excessive wear.

(Production Method of Intraoral Device 10)

The intraoral device 10 of this embodiment can be fabricated by a known method practiced in dental technology, for example.

Intraoral Device 20 According to Embodiment 2

Figure 6A:
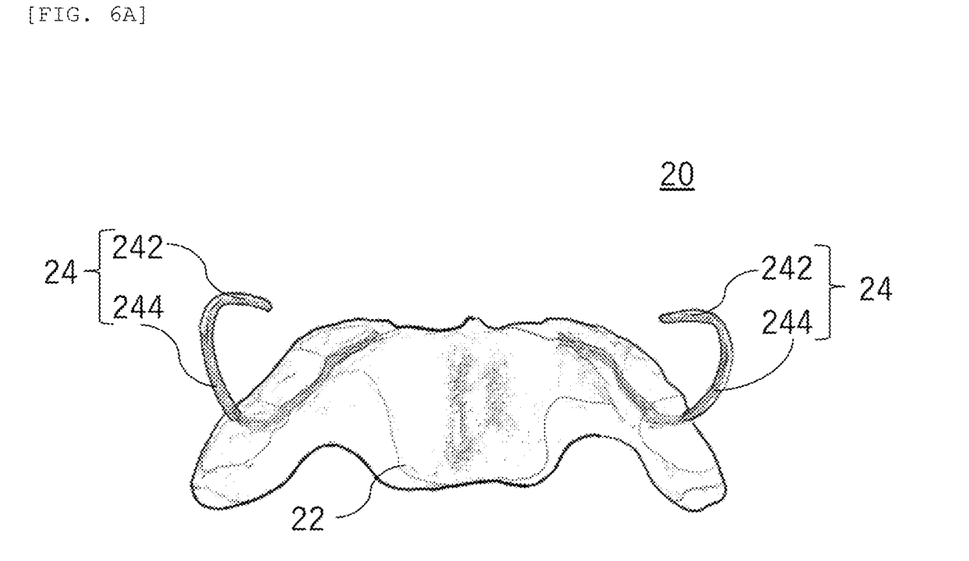
FIG. 6A is a rear view illustrating an intraoral device 20 according to Embodiment 2 (viewed from the palatal side).
Figure 6B:
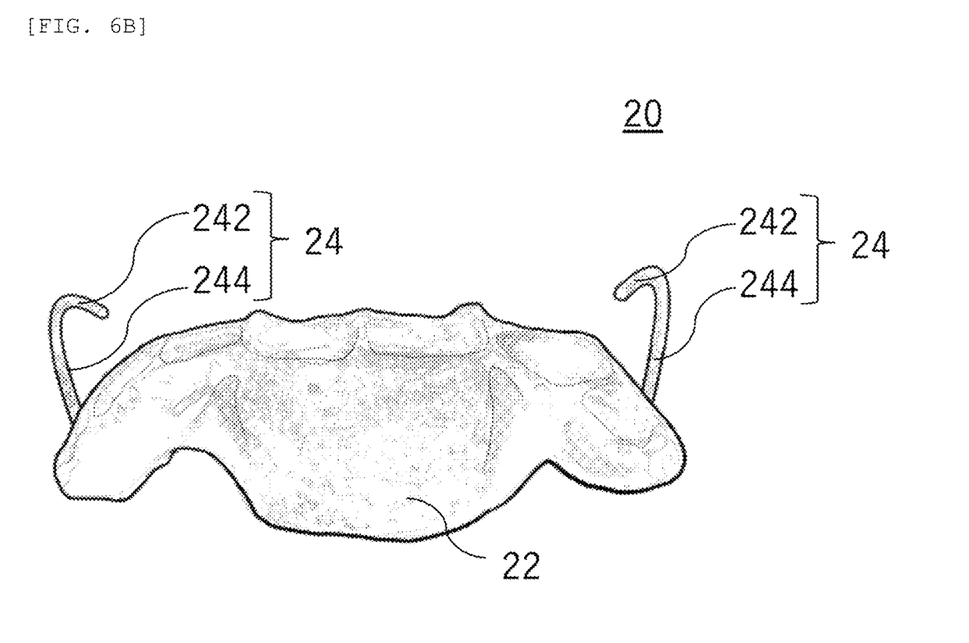
FIG. 6B is a front view illustrating the intraoral device 20 according to Embodiment 2 (viewed from the labial side).
Figure 6C:
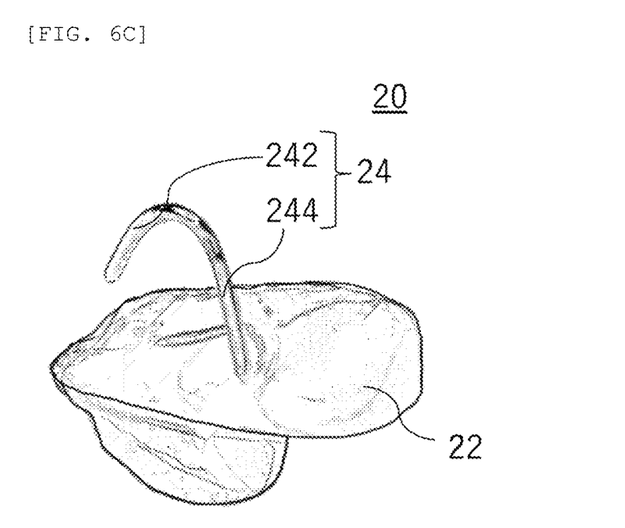
FIG. 6C is a side view illustrating the intraoral device 20 according to Embodiment 2.
Figure 6D:
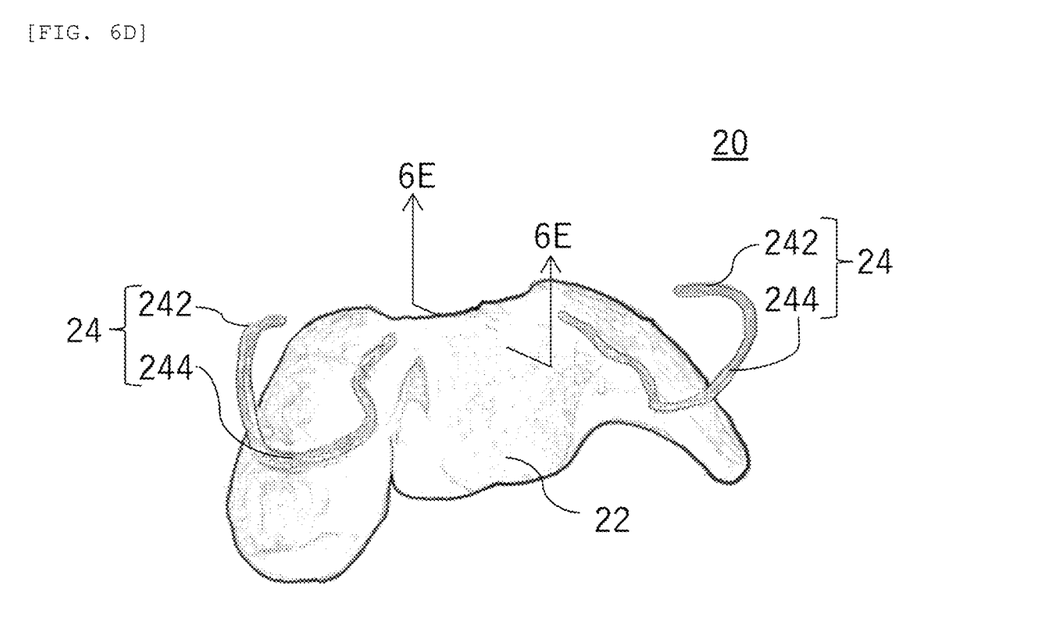
FIG. 6D is a perspective view illustrating the intraoral device 20 according to Embodiment 2.
Figure 6E:
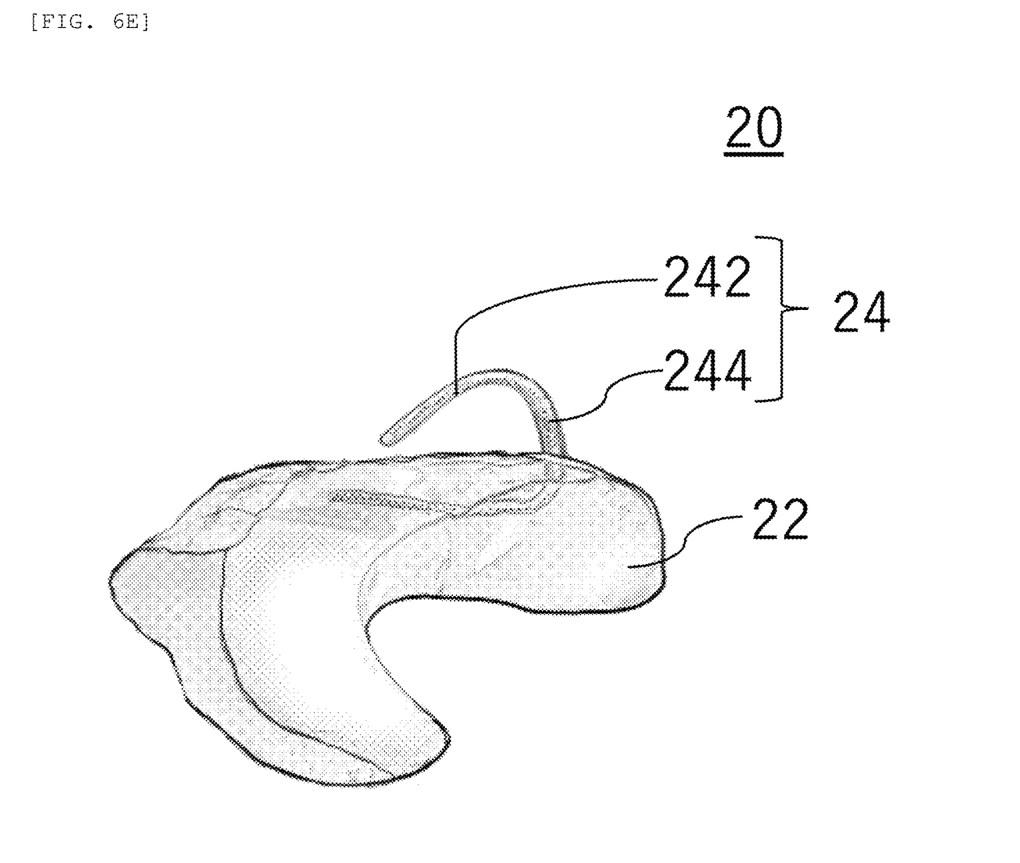
FIG. 6E is a cross-sectional view along line 6E-6E in FIG. 6D.

FIG. 6A is a rear view illustrating an intraoral device 20 according to Embodiment 2 (viewed from the palatal side). FIG. 6B is a front view illustrating the intraoral device 20 according to Embodiment 2 (viewed from the labial side). FIG. 6C is a side view illustrating the intraoral device 20 according to Embodiment 2. FIG. 6D is a perspective view illustrating the intraoral device 20 according to Embodiment 2. FIG. 6E is a cross-sectional view along line 6E-6E in FIG. 6D. As shown in FIG. 6A to FIG. 6E, the intraoral device 20 according to Embodiment 2 is different from the intraoral device 10 according to Embodiment 1 in the shape of the hook 242. As shown, the hook 242 is not limited to the ball clasp illustrated in Embodiment 1 and may take various other shapes.

Embodiments 1 and 2 have been described above. Cases of poor dental alignment are increasing in recent years due to the change in dietary and eating habits. When the teeth are poorly aligned, the teeth fall toward the tongue, reducing the volume of the oral cavity volume and causing the teeth to hit the tongue. Thereby, the tongue feels stress, and the tongue retracts posteriorly from its position where it should be (where the tongue naturally makes contact with the maxilla) and creates a gap that allows oral breathing between the tongue and the maxilla. With the intraoral device 10 or 20 described above, the posteriorly displaced tongue 300 can be brought to and kept in its position where it should be (where the tongue 300 naturally makes contact with the maxilla).

The intraoral device 10 or 20 makes oral breathing harder and facilitates nasal breathing. Therefore, the user of the intraoral device 10 or 20 can make a habit of having the tongue 300 in contact with the maxilla and establish the habit of nasal breathing.

Habitual nasal breathing leads to oral moisturization with saliva, which prevents dental diseases, as well as helps improve various symptoms of dermal diseases, allergies, and sleep disorders (snoring), etc. Therefore, the intraoral device 10 or 20 is effective for improvement of various symptoms.

With the spread of the COVID19 in recent years, more and more people find it hard to breathe through the nose due to the mask and tend to breathe through the mouth. In this respect, the intraoral device 10 or 20 that can help the user to habitually breathe through the nose and close the mouth tight is particularly effective.

The intraoral device 10 or 20 can also be used to correct a tongue habit (movement of the tongue 300 pressed against the teeth, resulting in an unconscious tongue thrust from between the teeth), or develop a correct swallowing habit.

The intraoral device 10 or 20 can also help the user make a habit to position the mandible that has retracted posteriorly at a more anterior and superior position and to have the tongue 300 in tight contact with the palate. This allows the user to habitually breathe through the nose, which can improve snoring, or enable treatment of sleep apnea syndrome.

While embodiments of the present invention have been described above, the description relates to one example of the present invention and should not limit the present invention in any way.

The user of the intraoral device according to the present invention should preferably seek regular maintenance by a dentist (e.g., regular check-up). This is because, in using the intraoral device inside the oral cavity, it is preferable to constantly maintain a favorable intraoral environment.

REFERENCE SIGNS LIST 10, 20 Intraoral device
12, 22 Main body
14, 24 Locking device
142, 242 Hook
144, 244 Leg portion
S1 First region
S2 Second region
S3 Third region
300 Tongue

The invention claimed is:

1. An intraoral device comprising a continuous main body to be attached to a plurality of maxillary teeth in a mouth at once, wherein:
   the continuous main body includes a first region, a second region, and a third region,
   the first region is configured to be provided in a position where a mandible cannot be retracted further posteriorly, and the first region is configured to be in contact with mandibular anterior teeth at this position,
   the continuous main body has a shape configured to conform to a lingual interface between crown and gingiva of maxillary teeth to which the main body is attached, an incisive papilla being configured to be exposed from the continuous main body,
   the first, second, and third regions being configured such that the mandibular anterior teeth, after being brought into contact with the first region, are moved to make contact with the second region with a closing of the mouth with the mandibular anterior teeth in contact with the continuous main body, and successively moved with the closing of the mouth with the mandibular anterior teeth in contact with the continuous main body to make contact with the third region, thereby causing the mandible to move anteriorly and superiorly while at least a portion of the mandibular anterior teeth remain positioned posteriorly to the maxillary anterior teeth when in contact with the third region,
   the continuous main body is configured to be inclined toward the mandible from the third region to the first region so that a space is formed between a lingual side face of the continuous main body and a palate, and after the mandible is configured to be moved anteriorly and superiorly, incisive papilla are configured to be exposed from the continuous main body and on the lingual side face of the continuous main body such that when a distal end portion of a tongue is placed on the incisive papilla the tongue is allowed to make contact with the palate, and
   wherein the intraoral device is configured to be attached inside the mouth such that an anterior side and bottom end of maxillary anterior teeth are exposed.

2. The intraoral device according to claim 1, wherein the intraoral device is configured to be attached inside the mouth such that the mouth is allowed to be closed.

3. The intraoral device according to claim 1, comprising a locking device that includes
   a hook configured to be engaged with an undercut that exists in a direction of attachment and removal of the continuous main body, and
   a leg portion extending from the hook and embedded in the continuous main body, with the leg portion being embedded in the continuous main body at a point configured to be higher than a lingual crown center of a maxillary tooth on a palatal side, and passing through a point configured to be higher than the lingual crown center of the maxillary tooth on the palatal side while being embedded in the continuous main body, and moreover terminating at a point configured to be higher than the lingual crown center of the maxillary tooth on the palatal side.

4. The intraoral device according to claim 1, wherein the continuous main body is configured to be attached to teeth from a maxillary right first or second premolar to a maxillary left first or second premolar.

5. The intraoral device according to claim 1, wherein the continuous main body is made of resin.

* * * * *